US007229051B2

(12) United States Patent
Mailhot, Jr.

(10) Patent No.: US 7,229,051 B2
(45) Date of Patent: Jun. 12, 2007

(54) SUPPORT DEVICE FOR GUIDEWIRES AND CATHETERS AND METHOD OF USE THEREOF

(76) Inventor: Robert Mailhot, Jr., 4874 Côte-des-Neiges, F-501, Montréal, Quebec (CA) H3V 1H4

(*) Notice: Subject to any disclaimer, the term of this patent is extended or adjusted under 35 U.S.C. 154(b) by 188 days.

(21) Appl. No.: 11/056,099

(22) Filed: Feb. 14, 2005

(65) Prior Publication Data
US 2006/0180714 A1 Aug. 17, 2006

(51) Int. Cl.
*F16L 3/00* (2006.01)
(52) U.S. Cl. .............. 248/51; 248/52; 248/58; 248/62; 248/316.7; 248/205.2; 248/73; 248/690; 248/683; 248/205.3; 248/684; 248/300; 248/56; 248/57; 248/63; 248/65; 211/85.13; 211/70.6; 211/73; 604/174; 604/180; 604/523; 606/129; 5/658; 5/503.1; 24/115 R; 24/129 R; 24/910; 24/130; 24/129 B; 24/129 A; 24/570; D6/553
(58) Field of Classification Search ............ 248/51, 248/52, 58, 62, 316.7, 205.2, 73, 690, 683, 248/205.3, 684, 300, 56, 57, 63, 65, 68.1, 248/650; 38/104; D6/553; 174/48, 170; 211/85.13, 70.6, 73; 604/174, 180, 523; 128/DIG. 6, DIG. 26; 606/129; 24/129 R, 24/910, 130, 129 B, 129 A, 570, 115 R; 5/658, 503.1

See application file for complete search history.

(56) References Cited

U.S. PATENT DOCUMENTS

| | | | | |
|---|---|---|---|---|
| 1,759,591 A | * | 5/1930 | Pleister et al. ........... 24/115 M |
| D87,702 S | * | 9/1932 | Aufiero ....................... D8/366 |
| 2,014,052 A | * | 9/1935 | Obermeyer ................. 24/570 |
| 2,365,467 A | * | 12/1944 | Hammerstein ........... 248/117.2 |
| 2,459,692 A | * | 1/1949 | Fletcher ........................ 248/50 |
| 2,561,311 A | * | 7/1951 | Homann ....................... 248/73 |
| 3,179,991 A | | 4/1965 | Seal |
| 3,286,713 A | * | 11/1966 | Kurtz et al. ................ 604/180 |
| 3,350,830 A | * | 11/1967 | Smith, Jr. et al. ............ 52/509 |
| 3,414,219 A | * | 12/1968 | Siegel .......................... 248/65 |
| 3,802,654 A | * | 4/1974 | Jenko et al. .................. 248/73 |
| 3,962,757 A | * | 6/1976 | Gedney ........................ 24/562 |
| 4,163,372 A | * | 8/1979 | Frye et al. ................. 62/259.1 |
| 4,164,975 A | * | 8/1979 | Bottum ........................ 165/68 |
| 4,520,518 A | * | 6/1985 | Reaser .......................... 5/498 |
| 4,794,660 A | * | 1/1989 | Hawkrigg ...................... 5/498 |
| 4,795,121 A | * | 1/1989 | Comito ....................... 248/314 |
| 4,871,074 A | * | 10/1989 | Bryson et al. ................ 211/26 |
| D305,083 S | * | 12/1989 | White ......................... D6/526 |
| 4,967,434 A | * | 11/1990 | Hill ............................... 5/658 |

(Continued)

*Primary Examiner*—Cari D. Friedman
*Assistant Examiner*—Nkeisha J. Dumas
(74) *Attorney, Agent, or Firm*—Louis Martineau

(57) ABSTRACT

A support device for supporting at least one medical wire adjacent a supporting surface. The support device comprises a plate-shaped holder portion defining a peripheral edge, the holder portion comprising a support slot defining a loading opening made in the peripheral edge of the holder portion, a holder well made transversely in the holder portion spacedly from its peripheral edge, and a channel made transversely in the holder portion and extending between the holder well and the loading opening. The holder well is dimensioned such that it is broader than the medical wire the support device is destined to support. The support device further comprises attachment means connected to the holder portion for attaching the support device to the supporting surface.

5 Claims, 3 Drawing Sheets

U.S. PATENT DOCUMENTS

| | | | |
|---|---|---|---|
| 5,027,494 A * | 7/1991 | Martin | 29/402.15 |
| 5,102,399 A | 4/1992 | Chu | |
| 5,267,710 A * | 12/1993 | Condon | 248/65 |
| 5,323,992 A | 6/1994 | Sifers et al. | |
| 5,370,345 A * | 12/1994 | Condon | 248/65 |
| 5,417,401 A * | 5/1995 | Thompson et al. | 248/674 |
| 5,620,092 A * | 4/1997 | Meisinger | 206/376 |
| 5,730,522 A * | 3/1998 | Wyke et al. | 362/432 |
| 5,769,786 A | 6/1998 | Wiegel | |
| 6,047,825 A | 4/2000 | Samuels | |
| 6,176,852 B1 | 1/2001 | Ischinger | |
| 6,375,006 B1 | 4/2002 | Samuels | |
| 6,457,194 B1 * | 10/2002 | Bennett | 5/504.1 |
| 6,508,447 B1 * | 1/2003 | Catani et al. | 248/300 |
| 6,523,791 B2 * | 2/2003 | Bernard et al. | 248/68.1 |
| 6,669,156 B2 * | 12/2003 | East et al. | 248/300 |
| 2001/0010110 A1 * | 8/2001 | Matsushima et al. | 24/130 |
| 2003/0132352 A1 * | 7/2003 | Weaver | 248/68.1 |
| 2004/0019302 A1 | 1/2004 | Williams et al. | |
| 2004/0094681 A1 * | 5/2004 | Birnbaum | 248/300 |
| 2004/0256528 A1 * | 12/2004 | Sanatgar et al. | 248/300 |

\* cited by examiner

SUPPORT DEVICE FOR GUIDEWIRES AND CATHETERS AND METHOD OF USE THEREOF

FIELD OF THE INVENTION

The present invention relates to support devices, and more particularly to a support device for supporting medical wires such as guidewires and catheters, during medical procedures.

BACKGROUND OF THE INVENTION

Guidewires and catheters are used in a variety of different medical procedures, for example during angiographic, endovascular or surgical procedures. For example, guidewires are used to position catheters in a lumen of a patient body, such as the patient's vasculature for example. When guidewires are used in such medical procedures, a leading end portion of the guidewire is normally introduced into the patient's body through a naturally occurring orifice, or an incision, or the like. After having been introduced into the patient's body, the leading end portion of the guidewire is navigated through body lumens until a leading end of the guidewire is positioned at an area of interest. A catheter can then be slipped around the pre-positioned guidewire, inserted and navigated in the patient's lumens towards the area of interest while sliding around and being guided by the pre-positioned guidewire. Accordingly, support device 10 can be self-standing.

A guidewire positioned in the patient's lumens can be used for positioning more than one catheter in the patient. Indeed, once a given catheter has been utilized to serve its particular function, it can be pulled out of the patient's body, and another catheter having a different function can be slipped around and slid along the pre-positioned guidewire, in order to reach the area of interest in the patient's lumens.

After the catheter-surrounded guidewire is appropriately positioned within the patient's body, a loose trailing end portion thereof typically extends out of the patient's body from its point of entry. It has been found that the loose trailing end portion of the guidewire extending outside the patient's body can be difficult to manage and can disturb the medical staff performing the medical intervention. This is especially true when more than one guidewire is being used during the medical procedure.

Therefore, the use of means for supporting the trailing end of guidewires and catheters during medical procedures is desirable. Devices for supporting the trailing end of guidewires and catheters exist, but lack versatility.

SUMMARY OF THE INVENTION

The present invention relates to a support device for supporting at least one medical wire adjacent a supporting surface, comprising:

a plate-shaped holder portion defining a peripheral edge, said holder portion comprising a support slot defining a loading opening made in said peripheral edge, a holder well made transversely in said holder portion spacedly from said peripheral edge, said support slot further comprising a channel made transversely in said holder portion and extending between said holder well and said loading opening, said channel opening at a first end into said holder well and opening at a second end outwardly of said holder portion at said loading opening; said holder well being dimensioned such that it is broader than the medical wire said support device is destined to be used with; and attachment means connected to said holder portion for attaching said support device to the supporting surface;

wherein a section of a medical wire may be inserted in said loading opening and along said channel in order enter into said holder well and to be supported therein.

In one embodiment, the support device further comprises a plate-shaped base portion connected transversely to said holder portion, said base portion being destined to rest against the supporting surface, said support being self-standing.

In one embodiment, said support device is for attachment to a sheet-covered surface, and said attachment means comprise a sheet wedging slot in said base portion, said sheet wedging slot being for wedging a fold of the sheet covering the sheet-covered surface therein.

In one embodiment, said wedging slot also extends coextensively in said holder portion.

In one embodiment, said holder portion and base portion of said support device are orthogonally connected to one another form a L-shaped structure.

In one embodiment, said support device is a one-piece structure.

In one embodiment, said channel is dimensioned so as to be slightly wider than the medical wire said support device is destined to be used with.

The present invention also relates to a method of use of a support device for use during medical procedures, said support device being of the type comprising:

a plate-shaped holder portion defining a peripheral edge, said holder portion comprising a support slot defining a loading opening made in said peripheral edge, a holder well made transversely in said holder portion spacedly from said peripheral edge, said support slot further comprising a channel made transversely in said holder portion and extending between said holder well and said loading opening, said channel opening at a first end into said holder well and opening at a second end outwardly of said holder portion at said loading opening; said holder well being dimensioned such that it is broader than the medical wire said support device is destined to be used with; and attachment means connected to said holder portion for attaching said support device to a supporting surface;

wherein said support device is for supporting trailing end portions of at least one guidewire and of at least one catheter to be connected at their leading end portions to a patient's body, said method of use comprising the steps of:

a) attaching said support device to a supporting surface with said attachment means;
b) inserting said guidewire trailing end portion inside said loading opening of said support device, circulating said guidewire trailing end portion along said channel and entering it into said holder well in order for it to be supported therein; and
c) slipping said catheter on a trailing end of said guidewire, sliding said catheter along said guidewire trailing end portion through and past said holder well of said support device.

In one embodiment, said method comprises the following additional step:

d) repeating steps b) and c) with a second guidewire and a second catheter to support said second guidewire and said second catheter in said support device.

DETAILED DESCRIPTION OF THE EMBODIMENTS

Figure 1:
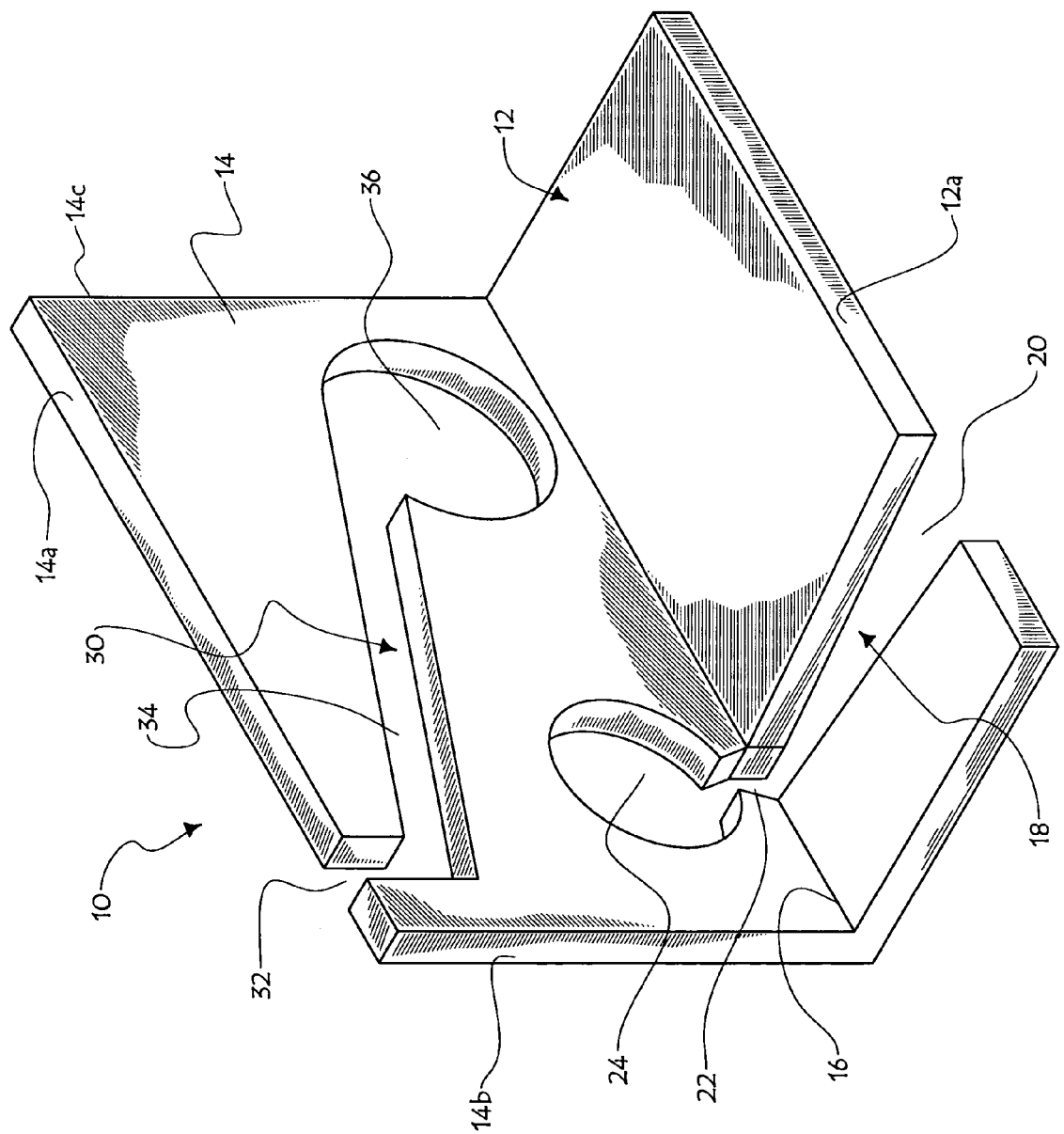
FIG. 1 shows a perspective view of a medical wire support device according to the present invention.

FIG. 1 shows a support device 10 according to the present invention, which purpose is to support medical wires. The expression "medical wire" will be used herein as incorporating all kinds of wire-shaped implements used during medical procedures, in particular guidewires and catheters.

In the embodiments shown in the drawings, medical wire support device 10 is a generally L-shaped one-piece structure. Support device 10 comprises a plate-shaped base portion 12, of rectangular shape for example, and which forms the member upon which medical wire support device 10 will rest. Support device 10 further comprises a holder portion 14 integrally connected to base portion 12 transversely thereto; base portion 12 and holder portion 14 intersect at the corner 16 of the L-shaped support device 10. In one embodiment, corner 16 makes a right angle between portions 12 and 14.

Figure 2:
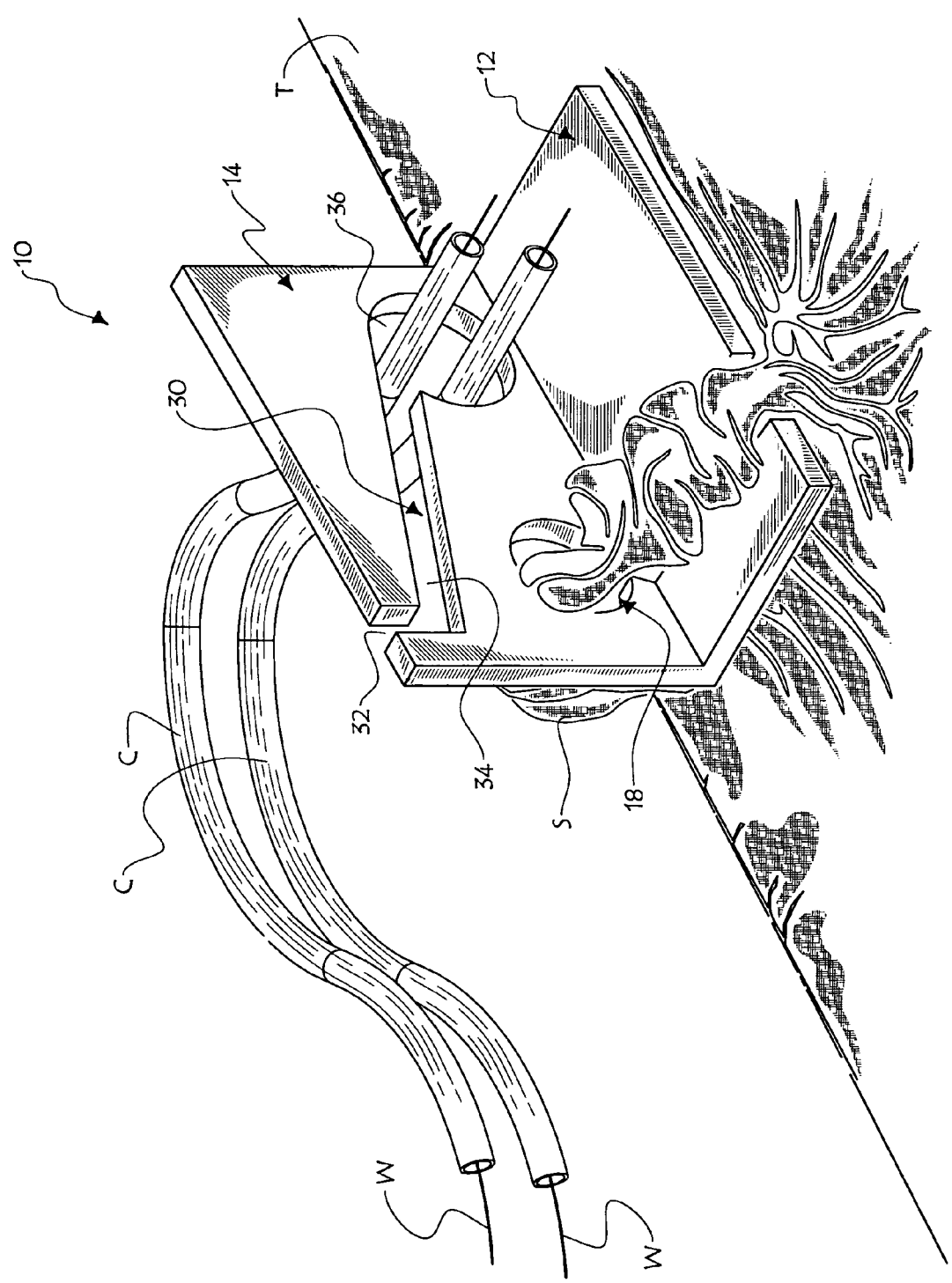
FIG. 2 shows a perspective view of the medical wire support device of FIG. 1 installed on a sheet-covered surgical table.
Figure 3:
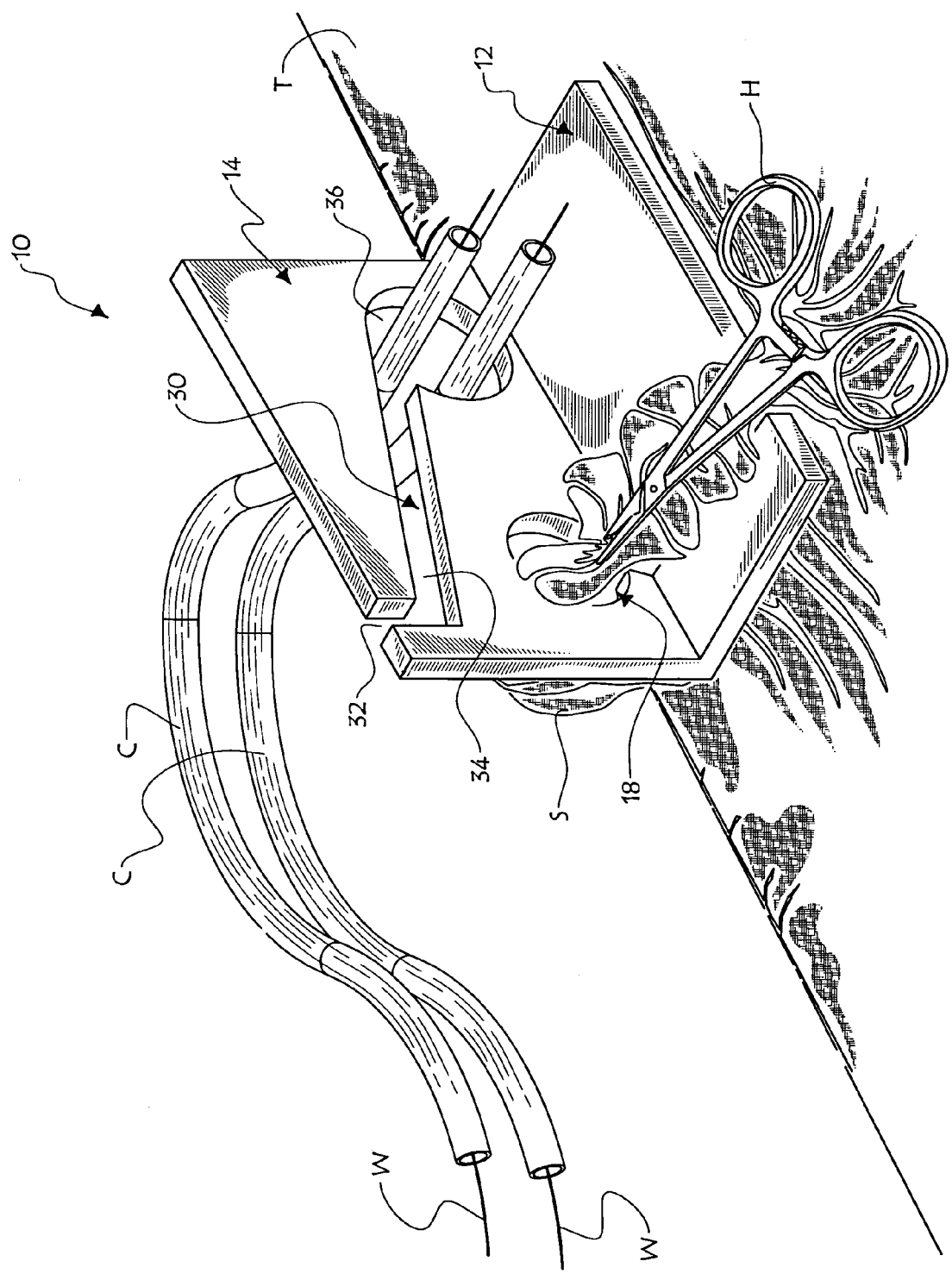
FIG. 3 shows a view similar to that of FIG. 2, and further shows a hemostat pinching the sheet of the surgical table to secure the medical wire support device to the surgical table.

Support device 10 comprises attachment means enabling its attachment to a supporting surface, such as an surgical table for example (as shown in FIGS. 2-3). In the embodiments of the figures, such attachment means comprise a sheet wedging slot 18 formed in medical wire support device 10. Wedging slot 18 defines a first slot portion 20 made transversely across base portion 12, and tapering from a widest end at the outer free edge 12a of base portion 12 towards a narrowest end at corner 16. Moreover, first slot portion 20 tapers towards a bottleneck portion 22 formed in corner 16, which in turn opens to a generally round aperture 24 made transversely through upstanding holder portion 14 of support device 10. When used atop a sheet-covered surgical table, medical wire support device 10 is releasably attached thereto by wedging a two-layers fold of the sheet inside the wedging slot 18, as illustrated in FIG. 2, the fold of the sheet being squeezed in bottleneck portion 22 of the slot 18 and the ridge of the fold being allowed to crease up and fill the round aperture 24 of wedging slot 18.

Of course, medical wire support device 10 could be provided with alternate attachment means, allowing for example its attachment to non-horizontal surfaces, or its attachment to supporting surface which are not covered with a sheet such as the instrument table.

Moreover, support device 10 is provided with separate means for supporting a number of medical wires. These means, according to the present invention, comprise a support slot 30 made transversely through holder portion 14. Support slot 30 comprises a serial-load channel 34, which at one end opens outwardly of support device 10 at a loading opening 32 made in the peripheral edge of holder portion 14, for example in its outer free edge 14a opposite portion 22 as shown in the figures. Serial-load channel 34 opens at a second opposite end to a holder well 36 formed in plate-shaped holder portion 14 spacedly from the latter's peripheral edge. Holder well 36 is dimensioned so as to be much broader than the catheters the support device 10 is destined to be used with, and serial-load channel 34 is dimensioned to be just slightly wider than the catheters the support device 10 is destined to be used with, for reasons described hereinafter.

It is noted that in the embodiment of the figures, loading opening 32 is positioned adjacent one lateral edge 14b of plate-shaped holder portion 14, and serial-load channel 34 slants downwardly therefrom towards the opposite lateral edge 14c adjacent which holder well 36 is located. The invention should however not be limited to such a configuration of support slot 30. For example, the holder well could be differently shaped.

When support device 10 is in use, its base portion 12 rests flatly against a work area such as the instrument table or the surgical table on which the patient lays. The embodiment of medical wire support device 10 shown in the present figures is for use on an surgical table T covered with a sheet S. When in use (FIG. 2), support device 10 is releasably secured on the surgical table T by wedging a fold of the sheet S covering table T in sheet wedging slot 18 made in support device Optionally, a hemostat H (FIG. 3), commonly used in vascular surgery, or any other kind of pinching device such as a "kelly device", can be used to pinch the fold of sheet S wedged in slot 18 and passing therethrough, in order to prevent accidental release and disengagement of the sheet S from the wedging slot 18 and thus prevent unfastening of medical wire support device 10 from the underlying surgical table T.

When the support device 10 is fastened to the surgical table T, medical wires such as guidewires W and catheters C can be supported in the support slot 30 of its plate-shaped holder portion 14. For example, during a medical procedure where a guidewire W needs to be used, it is transversely inserted in the wire loading opening 32, and circulated along channel 34 until it reaches holder well 36. The trailing end portion of guidewire W being at this point supported by medical wire support device 10, its leading end portion can then be manipulated and inserted in a lumen of the patient's body.

Guidewires are generally used to position catheters in the lumen of a patients body. Thus, once the trailing end portion of the guidewire W is supported in the support device 10, and its leading end portion has been positioned in the patient's body, a catheter C can be slipped on the guidewire W. To do so, no need to remove the guidewire W from the support. Holder portion 14 being plate-shaped and relatively thin, and holder well 36 being much broader than catheter C, catheter C can be directly slipped on the trailing end of the guidewire engaged in support device 10, and easily pass through the holder well 36 of support device 10, and towards the patients body. The catheter-surrounded guidewire is then supported in the support device 10, for example by bearing against the bottom trough of holder well 36.

The fact that the support of the present invention allows a catheter to be slipped on or off a guidewire while it remains in the patients body, and this without having to disengage the guidewire from the support, is especially advantageous. Indeed, guidewires are tricky to handle: they are extremely thin and barely visible to the naked eye; they are made from a very flexible material, all the while being very rigid and having a "springy" feel when handled. Moreover, guidewires generally comprise a slippery coating to ease they sliding navigation in the lumens of a patient's body. Accordingly, an important risk exists that at least a portion of the guidewire falls off the surgical table if it is not supported adequately when handled. Moreover, when handling a guidewire that is already installed in a patient's body to interchange catheters thereon, it is of course highly undesirable that the guidewire falls off the surgical table and touch the floor, since it would bring about microbial contamination of the guidewire and thus the need to remove the guidewire from the patient's body and replace it by a new, uncontaminated one. The support of present invention enables the practitioner to obviate this problem, as it allows the guidewire to remain engaged in and supported by the medical wire support device 10 while interchanging catheters thereon.

Moreover, holder well 36 is large enough to accommodate more than one catheter-surrounded guidewires. In FIGS. 2-3, support device 10 is shown to support two catheter-surrounded guidewires.

Also, the shape and configuration of support slot 30 is such that accidental disengagement of catheter-surrounded guidewires from the support device 10 is unlikely. Indeed, serial-load channel 34 is dimensioned to be just slightly wider than the catheters the support device 10 is destined to be used with, and consequently, the catheter-surrounded guidewires can only be manually extracted one at a time from support slot 30. Moreover, when the support device is laid horizontally as shown in the figures, if the catheter-surrounded guidewire accidentally egresses out of holder well 36 and passes into serial-load channel 34 during handling of the wire, it will eventually naturally slide along the downwardly slanted channel 34 back into holder well 36 under the bias of gravity. This effect can also be achieved if the support device 10 is disposed and attached to the supporting surface in a vertical disposition (not shown in the figures). It simply needs to be disposed such that the channel 34 be located at a higher level that holder well 36, so that if the wire accidentally egresses out of the holder well 36 and come into channel 34, it would naturally fall back into holder well 36 under the influence of gravity. It is noted that if held in a vertical position against a sheet-covered supporting surface, the support device of the embodiment illustrated in the appended figures would need to be used in conjunction with a pinching device such as a hemostat to keep it secured to the sheet covering the vertical supporting surface.

It is understood that multiple medical wire support devices 10 could be used in conjunction to ensure the support of the trailing end portion of medical wires such as catheter-surrounded guidewires. For example, where the trailing end portion of the medical wire extending out of a patient's body is substantially long, it may be desirable to support it using a number of support devices 10 spaced from each other along the length of the medical wire's trailing end portion.

A typical catheter C may have for example a diameter of 3 millimetres (mm) and a length of one meter. A typical guidewire W will have a similar length but be diametrically much smaller to fit inside the catheter's lumen, with a diameter of for example 0.5 mm.

The present device will be effective for example for use with:

guidewires use under the Seldinger technique (for arterial, venous or other percutaneous access);
most catheters for angiographic procedures (angiographic catheters, angioplasty catheters, embolization and work catheters);
elongated Swan-Ganz catheters;
Pacemaker electrodes;
etc.

The invention claimed is:

1. A support device for supporting at least one medical wire adjacent a supporting surface, comprising:
   a plate-shaped holder portion defining a peripheral edge said holder portion comprising a support slot defining a loading opening made in said peripheral edge, a holder well made transversely in said holder portion spacedly from said peripheral edge, said support slot further comprising a channel made transversely in said holder portion and extending between said holder well and said loading opening, said channel opening at a first end into said holder well and opening at a second end outwardly of said holder portion at said loading opening; and
   attachment means connected to said holder portion for attaching said support device to the supporting surface;
   wherein a section of a medical wire may be inserted in said loading opening and along said channel in order to enter into said holder well and to be supported therein;
   further comprising a plate-shaped base portion connected transversely to said holder portion, said base portion for resting against the supporting surface, wherein said support is self-standing:
   wherein said support device is for attachment to a sheet-covered surface, and said attachment means comprise a sheet wedging slot in said base portion, said sheet wedging slot being for wedging therein a fold of a sheet covering the sheet-covered surface; and
   wherein said wedging slot also extends coextensively in said holder portion.

2. A support device according to claim 1, wherein said holder portion and base portion of said support device are orthogonally connected to one another to form a L-shaped structure.

3. A support device according to claim 1, wherein said support device is a one-piece structure.

4. A support device according to claim 1, wherein said channel first portion is shorter than said channel second portion.

5. A support device according to claim 1, wherein said holder portion is rectangular and said peripheral edge comprises two lateral edges and an outer free edge, and wherein said loading opening is located on said outer free edge adjacently to a first one or said lateral edges, and said channel slants therefrom towards a second one of said lateral edges and away from said outer free edge.

* * * * *